United States Patent [19]

Foged et al.

[11] Patent Number: 5,470,850
[45] Date of Patent: Nov. 28, 1995

[54] 2,3,4,5-TETRAHYDRO-1H-3-BENZAZEPINES

[75] Inventors: Christian Foged, Birkerød; Rolf Holweg, Kvistgaard; Erik Nielsen, Væløse, all of Denmark

[73] Assignee: Novo Nordisk A/S, Bagsvaerd, Denmark

[21] Appl. No.: 238,996

[22] Filed: May 6, 1994

Related U.S. Application Data

[63] Continuation-in-part of Ser. No. 161,856, Dec. 3, 1993, abandoned, which is a continuation of Ser. No. 15,942, Feb. 10, 1993, abandoned.

[30] Foreign Application Priority Data

Feb. 24, 1992 [DK] Denmark .................................. 0233/92

[51] Int. Cl.$^6$ .................... C07D 405/02; C07D 405/10; A61K 31/55
[52] U.S. Cl. .......................... 514/213; 540/594; 540/595
[58] Field of Search .................................. 540/594, 595; 514/213

[56] References Cited

U.S. PATENT DOCUMENTS

| | | | |
|---|---|---|---|
| 4,255,445 | 3/1981 | Brush et al. | 424/285 |
| 4,751,222 | 6/1988 | Braestrup et al. | 514/213 |
| 5,017,571 | 5/1991 | Hansen et al. | 514/213 |

FOREIGN PATENT DOCUMENTS

| | | |
|---|---|---|
| 0200455 | 11/1986 | European Pat. Off. . |
| 0347672 | 12/1989 | European Pat. Off. . |
| 0383247 | 8/1990 | European Pat. Off. . |

OTHER PUBLICATIONS

Anderson et al., Life Science, vol. 37, pp. 1971–1983 (1985).
Hansen et al., Drug Metab. Dispos., vol. 20, No. 2, pp. 172–178 (1992).
Pedersen et al., Acta Pharmacol. Toxicol., vol. 31, pp. 488–496 (1972).

*Primary Examiner*—Philip I. Datlow
*Attorney, Agent, or Firm*—Steve T. Zelson; Cheryl H. Agris

[57] ABSTRACT

2,3,4,5-Tetrahydro-1H-3-benzazepines having the general formula

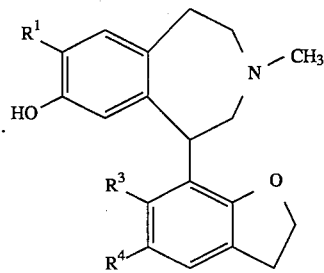

wherein
$R^1$ is Cl or Br; $R^3$ and $R^4$ are hydrogen, halogen, $CF^3$, CN, $NO_2$, or $NH_2$.

The compounds are useful in treatment of certain disorders in the central nervous system.

7 Claims, No Drawings

2,3,4,5-TETRAHYDRO-1H-3-BENZAZEPINES

This application is a continuation-in-part of application Ser. No. 08/161,856, filed Dec. 3, 1993, now abandoned which is a continuation of application Ser. No. 08/015,942, filed Feb. 10, 1993, now abandoned.

FIELD OF THE INVENTION

This invention relates to novel 2,3,4,5-tetrahydro-1H-3-benzazepines and pharmaceutically acceptable acid addition salts thereof, to methods for their preparation, to pharmaceutical compositions containing them, and to their use in the treatment of certain disorders in the central nervous system, e.g., psychosis, pain, depression, sleep disturbances, dyskinesias, Parkinson's disease, stroke.

BACKGROUND OF THE INVENTION

In the last decade intensive pharmacological research concerning benzazepines has taken place. The pharmacological properties of benzazepines depend to a large extent on the substituents. Various substituted benzazepines exhibiting neuroleptic, anti-aggressive, anti-Parkinson and vascular effects are known.

In European Patent No. 0 200 455 (Novo Industri A/S) 2,3,4,5-tetrahydro-1H-3-benzazepines having a heterocyclic or an ortho-fused heterocyclic ring system in the 5-position are described. These compounds are claimed to have antipsychotic and antidepressive effects.

SUMMARY OF THE INVENTION

It has now been found that a group of 5'- or 6'-substituted or 5',6'-disubstituted (2,3-dihydrobenzofuran-7-yl)-2,3,4,5-tetrahydro-1H-3-benzazepine compounds exhibit strong antidopaminergic effect which makes them useful in psychopharmaceutical applications.

Surprisingly, the compounds of the invention exhibit unexpectedly high oral antidopaminergic activity compared to known compounds.

According to the present invention there are provided 2,3,4,5-tetrahydro-1H-3-benzazepines of the general formula I

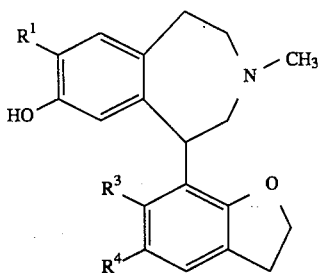

(I)

wherein
R$^1$ is Cl or Br;
R$^3$ and R$^4$ independently are hydrogen, halogen, CF$_3$, CN, NO$_2$ or NH$_2$ and pharmaceutically acceptable acid addition salts thereof, provided that R$^3$ and R$^4$ cannot be hydrogen at the same time.
Specific compounds of formula (I) are:
(+) 8-chloro-5-(5-bromo-2,3-dihydrobenzofuran-7-yl)-7-hydroxy-3-methyl- 2,3,4,5-tetrahydro-1H-2-benzazepine,
(+) 8-chloro-5-(2,3-dihydro-5-iodo-benzofuran-7-yl)-7-hydroxy-3-methyl- 2,3,4,5-tetrahydro-1H-3-benzazepine,
(+)8-chloro-5-(5,6-dichloro-2,3-dihydrobenzofuran-7-yl)-7-hydroxy-3-methyl- 2,3,4,5-tetrahydro-1H-3-benzazepine,
(+)8-chloro-5-(5-chloro-2,3-dihydrobenzofuran-7-yl)-7-hydroxy-3-methyl- 2,3,4,5-tetrahydro-1H-3-benzazepine,
8-chloro-5-(5-nitro-2,3-dihydrobenzofuran-7-yl)-7-hydroxy-3-methyl- 2,3,4,5-tetrahydro-1H-3-benzazepine,
8-chloro-5-(5-amino-2,3-dihydrobenzofuran-7-yl)-7-hydroxy-3-methyl- 2,3,4,5-tetrahydro-1H-3-benzazepine The compounds of formula I may be presented as a mixture of enantiomers, which may be resolved into the individual pure enantiomers. This resolution may conveniently be performed by fractional crystallization from various solvents, of the salts of compounds of the formula I with optical active acids or by other methods known from the literature, e.g. chiral column chromatography. Therefore, this invention includes all isomers, whether resolved or mixtures thereof.

Particularly valuable embodiments of this invention are non-toxic, pharmaceutically acceptable acid addition salts of benzazepines of formula I. Such salts include those derived from inorganic and organic acids such as hydrochloric, hydrobromic, sulphuric, phosphoric, methanesulfonic, acetic, lactic, maleic, phthalic and tartaric acids.

These salts may be prepared by methods known to professionals skilled in the art.

The invention also relates to compounds of formula I, wherein R$^3$ or R$^4$ is a radioactive isotope of iodine or bromine, such as the clinically used isotopes, $^{122}$I, $^{123}$I, $^{125}$I, $^{131}$I, $^{77}$Br, $^{82}$Br and $^{76}$Br. These compounds have been found useful as imaging agents in Single Photon Emission Computed Tomography (SPECT) or in Positron Emission Tomography (PET).

The invention further provides pharmaceutical compositions comprising the compounds of the invention. The dosage formulation will preferably contain the active compounds in the range of 0.1 mg to about 1000 mg for oral dosing. Typical dosage for antipsychotic effect would vary between about 0.5 to 10 mg/kg per day divided in 2 or 3 doses, administered orally.

DETAILED DESCRIPTION OF THE INVENTION

The compounds of the present invention can be prepared by various methods. These methods comprise:

a) halogenation of a compound of formula II

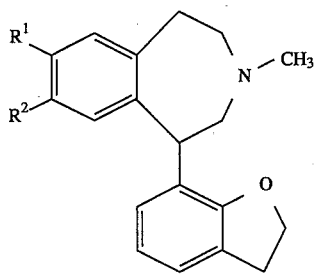

(II)

wherein R$^1$ is defined as above and R$^2$ is O—C$_{1-4}$-alkyl or O—CO—C$_{1-4}$-alkyl to form a compound of the general formula III

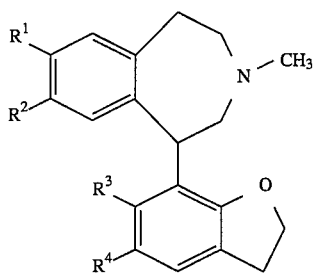

(III)

wherein $R^1$ and $R^2$ are defined as above, $R^3$ is halogen or H, $R^4$ is halogen, and deacylation or dealkylation of a compound of formula III to form a compound of formula I, wherein $R^1$, $R^3$ and $R^4$ are defined as above, b) nitration of a compound of formula II

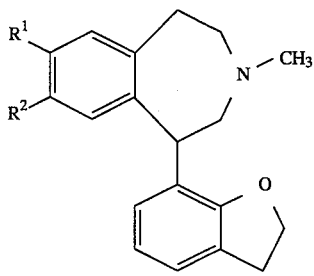

(II)

as defined in a) to form a compound of the general formula III,

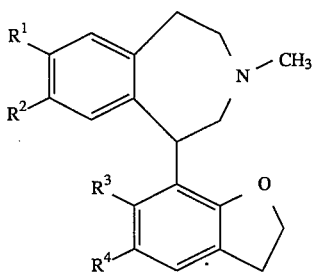

(III)

wherein $R^1$ and $R^2$ are defined as in a), $R^3$ is H and $R^4$ is —$NO_2$, and deacylation or dealkylation of a compound of formula III to form a compound of formula I, wherein $R^1$, $R^3$ and $R^4$ are as defined above or c) reduction or catalytic hydrogenation of a compound of formula IV,

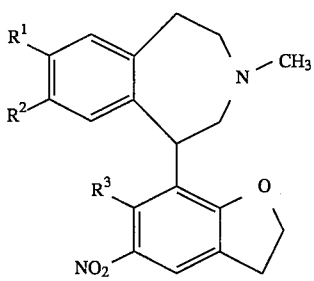

(IV)

wherein $R^1$ is defined as above, $R^2$ is O—$C_{1-4}$-alkyl or O—CO—$C_{1-4}$-alkyl and $R^3$ is H, to a compound of formula III,

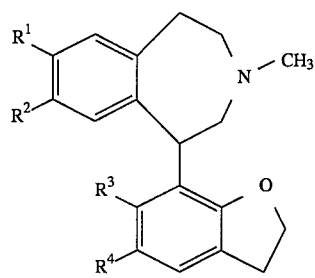

(III)

wherein $R^1$, $R^2$ and $R^3$ are defined as above and $R^4$ is —$NH_2$, and deacylation or dealkylation of the compound of formula III to form a compound of formula I, wherein $R^1$, $R^3$ and $R^4$ are defined as above;

d) diazotization followed by Sandmeyer reaction with copper cyanide of a compound of formula III as obtained in preparation method (c), followed by acidic deacylation of the product to form a compound of formula I wherein $R^1$ and $R^3$ are defined as above and $R^4$ is a cyano group;

e) reaction of a compound of formula III wherein $R^1$ is Cl, $R^2$ is O—$C_{1-4}$ alkyl and one of the groups $R^3$ or $R^4$ is Br, with trifluoromethyl iodide and copper powder in a solvent as DMF at elevated temperatures in a pressure vessel, essentially as described in D. Gaitanopoulos and M. Brenner, 1980, Synth. Commun. 10:213–219, leading to a compound of formula III wherein $R^1$ or $R^2$ are defined as above and $R^3$ or $R^4$ is $CF_3$, and subsequent de-O-alkylation employing pyridinium chloride at temperatures from 150° C. to 210° C., leading to a compound of formula I wherein $R^1$ is Cl and one of the groups of $R^3$ or $R^4$ is $CF_3$.

The starting materials employed in the synthesis of the compounds of formula I are known e.g. from European Patent No. EP 0.200.455.

The compounds of the invention are useful because of their pharmacological activity. In particular, the compounds of the invention are active in assays predictive for antipsychotic effect. Thus the compounds of formula I were tested for their binding to dopamine $D_1$ receptor in homogenates from rat striatum using the method described (Life Science vol. 37, p. 1971 (1985) P. Andersen et al.) and the result appears from Table I. $IC_{50}$ is the affinity of tested compounds for the dopamine $D_1$ receptor.

TABLE I

| Test Compound | $IC_{50}$ (nM) Dopamine $D_1$ receptor |
|---|---|
| Example No. 1 | 0.7 |
| Example No. 3 | 0.9 |

The previously mentioned high oral antidopaminergic activity of the compounds of the present invention in comparison to known compounds without the claimed 5'-substituents or 6'-substituents (EP 200.455) can be shown by calculating the ratio between oral ability to inhibit stereotyped behaviour in mouse following methylphenidate (i.e., Acta Pharmacol. Toxicol. 31, 1972, 488) and inhibition of $^3$H-SCH 23390 binding in vitro (measure of $D_1$-receptor antagonism). This yielded the following ratios shown in Table II:

TABLE II

| Test Compound | Index of oral mg/kg/ IC$_{50}$ SCH 23390 binding |
| --- | --- |
| Example no. 1 | 4 |
| Example no. 3 | 1.6 |
| Example no. 5 in EP 200.455 | 23 |

In Table II, "Example No. 5 in EP 200.455" is the (+) optical isomer of the compound disclosed in Braestrup (U.S. Pat. No. 4,751,222) at col. 4, lines 35–36 (compound 19) and In Example (column 9, lines 38–40).

The ratios shown in Table II are a measure of the oral potency of the compounds relative to their in vitro D-1 receptor affinity. A high ratio indicates poor oral effectiveness, whereas a low ratio indicates that low oral doses are effective relative to in vitro potency. Since a low oral effect is commonly seen with D-1 antagonistic benzazepines (e.g. Hansen et al., 1992, Drug Metab. Dispos. 20:172–178), the present invention describes improvements in oral potency relative to in vitro potency as indicated by the above ratios.

Therefore, the compound and composition of the present invention would be useful in treating a mental disorder related to a dysfunction of the dopamine D-1 receptor including but not limited to psychosis, pain, depression, sleep disturbances, dyskinesias, Parkinson's disease, stroke.

The compound of the invention, together with a conventional adjuvant, carder, or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form or sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing about 0.1–1000 mg of active ingredient or, more specifically, about 0.5–10 mg, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral administration, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically acceptable carrier per unit dosage.

A typical tablet, which may be prepared by conventional tabletting techniques, contains:

| | |
| --- | --- |
| Active compound | 1.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

EXAMPLES

The following examples illustrate the preparation of the novel compounds of this invention:

EXAMPLE 1

(+) 8-Chloro-5-(5-bromo-2,3-dihydrobenzofuran-7-yl)-7-hydroxy-3-methyl- 2,3,4,5-tetrahydro-1H-3-benzazepine a) (+) 8-Chloro-5-(2,3-dihydrobenzofuran-7-yl)-7-methoxy-3-methyl- 2,3,4,5-tetrahydro-1H-3-benzazepine (1.0 g, 2.9 mmol) was dissolved in acetic acid (10 ml). To the stirred solution was added bromine (0.20 ml, 4.0 mmol) in acetic acid (5 ml) over a period of 2 h. The mixture was stirred overnight at room temperature. A precipitate was formed. The white solid was filtered and washed with diethylether.

Yield 1.1 g (75%) of (+) 8-chloro-5-(5-bromo-2,3-dihydrobenzufuran-7-yl)- 7-methoxy-3-methyl-2,3,4,5-tetrahydro-1H-3-benzazepine, HBr as a white crystalline powder.

NMR 200 MHz $^1$H-chemical shifts in ppm of the free base. CDCl$_3$ as solvent, TMS as internal standard.

[δppm]: 2.42 (s,3H), 2.40–2.55 (m,1H), 2.95 (m,5H) 3.28 (t,2H), 3.70 (s, 3H), 4.43 (d,1H), 4.58 (t,2H), 6.38 (s,1H), 6.98 (d,1H), 7.18 (s, 1H), 7.26 (d,1H).

b) (+) 8-Chloro-5-(5-bromo-2,3-dihydrobenzofuran-7-yl)-7-methoxy-3-methyl2,3,4,5-tetrahydro-1H-3-benzazepine (3.9 g, 9.2 mmol) was dissolved in dichloromethane (50 ml). The solution was cooled on an icebath. To the stirred solution was added 10 vol % BBr$_3$ in dichloromethane (14 ml, 14.8 mmol). The reaction mixture was stirred for 2 h, and then warmed to room temperature. The mixture was added methanol and concentrated at reduced pressure. Methanol was added (50 ml) and the mixture was refluxed for 2 h, and then stirred at room temperature overnight. The mixture was concentrated to a thick oil. Methanol (15 ml) was added and under stirring NaOH (0.5M) was added until precipitation started. The mixture was stirred for one hour, then cooled on an icebath. The brown solid was filtered and washed with water.

Yield 3.2 g (85%) of the title compound as a crystalline slightly brown powder. NMR 200 MHz $^1$H-chemical shifts in ppm. of the free base. CDCl$_3$ as solvent, TMS as internal standard.

[δ, ppm]: 2.25 (t,1H), 2.35 (s,3H), 2.90 (m,5H), 3.22

(t,2H), 4.35 (d,1H), 4.51 (t,2H), 6.30 (s,1H), 6.96 (d,1H), 7.10 (s,1H), 7.22 (d,1H).

EXAMPLE 2

(+) 8-Chloro-5-(2,3-dihydro-5-iodo-benzofuran-7-yl)-7-hydroxy-3-methyl- 2,3,4,5-tetrahydro-1H-3-benzazepine a) Iodine (4.2 g, 16.3 mmol) and 32% peracetic acid (10.3 ml, 49 mmol) was stirred in acetic acid (50 ml) for 15 min. at room temperature. (+) 8-Chloro-5-( 2,3-dihydrobenzofuran-7-yl )-7-methoxy-3-methyl-2,3,4,5-tetrahydro-1H-3-benzazepine (5.6 g, 16.3 mmol) in acetic acid (50 ml) was added to the mixture over a period of 1 h. The mixture was stirred for additional 3 h. The mixture was treated with sodium thiosulfate and evaporated under reduced pressure to a brown solid. Dichloromethane was added and the organic phase was washed with water, NaOH (aq), water and then dried over anhydrous magnesium sulfate. The extract was filtered and concentrated to a brown solid. The product was purified by column chromatography (silica gel: $CH_2Cl_2$—MeOH).

Yield: 4.8 g (63%) of (+) 8-chloro-5-(2,3-dihydro-5-iodo-benzofuran-7-yl)- 7-methoxy-3-methyl-2,3,4,5-tetrahydro-1H-3-benzazepine as a Crystalline slightly brown powder.

NMR 200 MHz $^1$H-chemical shifts in ppm of the free base. $CDCl_3$ as solvent, TMS as internal standard.

[δppm]: 2.32 (m,1H), 2.36 (s,3H), 2.92 (m,5H), 3.22 (t,2H), 3.70 (s,3H), 4.37 (dd, 1H), 4.52 (t,2H), 6.35 (s,1H), 7.13 (broad s,2H), 7.42 (d,1H).

b. (+) 8-chloro-5-(2,3-dihydro-5-iodo-benzofuran-7-yl)-7-methoxy-3-methyl-2,3,4,5-tetrahydro-1H-3-benzazepine (300 mg, 0.65 mmol) was dissolved in dichloromethane (15 ml). To the stirred solution was added 10% $BBr_3$ in dichloromethane (2.0 ml, 2.1 mmol) over a period of 1 h. The mixture was stirred at room temperature for additionally 15 min. The mixture was diluted with methanol (25 ml) and concentrated at reduced pressure. Methanol (20 ml) was added, and under stirring NaOH (0.5M) was added until pH 7. The mixture was stirred for 1 h and water was added until precipitation started. The solid was filtered and washed with water.

Yield: 207 mg (70%) of the title compound as a crystalline slightly brown powder.

NMR 200 MHz $^1$H-chemical shifts in ppm of the free base. $CDCl_3$ as solvent, TMS as internal standard.

(δ, ppm): 2.28 (t,1H), 2.38 (s,3H), 2.90 (m,5H), 3.22 (t,2H), 4.37 (d,1H), 4.52 (t,2H), 6.30 (s,1H), 7.10 (s,1H), 7.18 (d,1H), 7.40 (d,1H).

EXAMPLE 3

(+)8-Chloro-5-(5,6-dichloro-2,3-dihydrobenzofuran-7-yl)-7-hydroxy-3-methyl-2,3,4,5-tetrahydro-1H-3-benzazepine 1.65 g (0.005 mole) (+)8-chloro-5-(2,3-dihydrobenzofuran-7-yl)-7-hydroxy- 3-methyl-2,3,4,5-tetrahydro-1H-3-benzazepine was dissolved in 2.5 ml acetic anhydride and left at room temperature for 1 h. The clear solution was concentrated in vacuo and repeatedly stripped with glacial acetic acid. Then the residue was redissolved in 10 ml acetic acid and 7.2 ml (0.0055 mole) of a 0.77 molar solution of chlorine in glacial acetic acid was slowly added to the stirred solution at room temperature. After 1 h another 7.1 ml of the chlorine solution was added. The reaction mixture was again stirred for 1 h. Then 20 ml ethanol and 1 ml concentrated HCl were added, and the mixture was refluxed for 1 h. After cooling, the solution was diluted with 20 ml ethanol and adjusted to pH 8 by careful addition of 10% $Na_2CO_3$ solution.

The crude product precipitated out spontaneously and was collected by filtration. Column chromatography (stationary phase: C18 silica; eluent: ammoniumsulfate/acetonitrile 70:30; pH 3.3) yielded the pure title compound. M.p.: 224°–225° C. $^1$H-NMR in $CDCl_3$ [δ, ppm]: 2.23 (t,1H); 2.40 (s,3H); 2.73 (dd,1H); 2.80–3.37 (m,6H); 4.57 (t,2H); 4.93 (d,1H); 6.17 (broad s,1H); 7.07 (s,1H); 7.25 (s,2H).

EXAMPLE 4

(+)8-Chloro-5-(5-chloro-2,3-dihydrobenzofuran-7-yl)-7-hydroxy-3-methyl- 2,3,4,5-tetrahydro-1H-3-benzazepine The synthesis and workup followed essentially the method described in example 3, with the only difference that 1.1 equivalent of chlorine was used for the chlorination.

The crude product was chromatographically purified as described above and yielded the free base as a crystalline powder. M.p.: 182°–186° C.

$^1$H-NMR in $CDCl_3$ [δ, ppm]2.40 (s,3H); 2.30–3.20 (m,8H); 3.90 (dd, 1H); 4.15 (t,2H); 5.96 (s,1H); 6.40 (d,1H); 6.65 (s,1H); 6.70 (d,1H).

EXAMPLE 5

8-Chloro-5-(5-nitro-2,3-dihydrobenzofuran-7-yl)-7-hydroxy-3-methyl- 2,3,4,5-tetrahydro-1H-3-benzazepine a) 1.50 g (0.00386 mole) 8-chloro-5-(2,3-dihydrobenzofuran-7-yl)-7-methoxy-3-methyl-2,3,4,5-tetrahydro-1H-3-benzazepine was dissolved in 20 ml acetic acid. 2.80 g (0.0116 mole) copper nitrate trihydrate was added and the mixture was stirred at room temperature for 18 h. The solvent was evaporated in vacuo, the residue treated with aqueous ammonia and extracted with dichloromethane. The solution was washed with water and brine, concentrated in vacuo and the residue redissolved in ether. Unsoluble impurities were removed by filtration and 8-chloro-5-(5-nitro- 2,3-dihydrobenzofuran-7-yl)-7-methoxy-3-methyl-2,3,4,5-tetrahydro-1H-3-benzazepine was obtained as the hydrochloride by adding an excess of a HCl solution in ether and collecting the precipitate by filtration. White crystals. M.p.: 251°–254°C.

$^1$H-NMR of the free base in $CDCl_3$ [δ, ppm]: 2.37 (s,3H); 2.40–3.25 (m,6H); 3.34 (t,2H); 3.70 (s,3H); 4.45 (d,1H); 4.73 (t,2H); 6.36 (s,1H); 7.20 (s,1H); 7.86 (d,1H); 8.03 (d,1H).

b) 0.220 g (0.00052 mole) 8-chloro-5-(5-nitro-2,3:dihydrobenzofuran-7-yl)- 7-methoxy-3-methyl-2,3,4,5-tetrahydro-1H-3-benzazepine hydrochloride was dissolved in 10 ml dry dichloromethane and cooled in an ice bath. To the stirred solution 5 ml of a 1 molar solution of boron trichloride in hexane was added. The reaction mixture was allowed to warm up to room temperature and was stirred for 4.5 h. Then the solution was cooled in an ice bath and hydrolized by carefully adding 15 ml methanol. The formed crystalline hydrochloride of the title compound was collected by filtration and dried.

Slightly pink crystalline powder. M.p.: 265°–270° C. under decomposition.

$^1$H-NMR in $d_6$-DMSO [δ, ppm]: 2.80 (d,3H); 2.85–3.85 (m,8H); 4.75 (t,2H); 4.90 (d,1H); 6.22 (s,1H); 7.27 (s,1H); 8.02 (d,1H); 8.25 (d,1H); 9.95 (s,1H); 11.30 (broad s,1H).

EXAMPLE 6

8-Chloro-5-(5-amino-2,3-dihydrobenzofuran-7-yl)-7-hydroxy-3-methyl- 2,3,4,5-tetrahydro-1H-3-benzazepine a) A stirred mixture of 2.50 g (0.011 mole) sodium sulfide and 0.60 g (0.011 mole) ammonium chloride in 10 ml n-propanol was warmed to reflux temperature and a solution of 0.44 g (0.0011 mole) 8-chloro-5-(5-nitro-2,3-dihydrobenzofuran-7-yl)-7-methoxy-3-methyl-2,3,4,5-tetrahydro-1H-3-benzazepine was added dropwise and reflux was continued for 16 h. The solvent was removed in vacuo and the residue was redissolved in dichloromethane. The solution was washed with 0.1N NaOH, water and brine. Evaporation yielded 8-chloro-5-(5-amino-2,3-dihydrobenzofuran-7-yl)- 7-methoxy-3-methyl-2,3,4,5-tetrahydro-1H-3-benzazepine as a foam.

$^1$H-NMR in CDCl$_3$[δ, ppm]: 2.37 (s,3H+m,1H); 2.75–3.30 (m,7H); 3.35 (broad s,2H); 3.68 (s,3H); 4.33 (t,1H); 4.46 (t,2H); 6.21 (d,1H); 6.43 (s,1H); 6.53 (d,1H); 7.12 (s,1H).

b) 2.8 ml (0.0056 mole) of a 2M solution of boron trichloride in dichloromethane was added to an icecold stirred solution of 200 mg (0.00056 mole) of the product of step a. in 10 ml dichloromethane. The reaction mixture was stirred for 8 h at room temperature and was then concentrated in vacuo. The residue was redissolved in ether, washed with saturated NaHCO$_3$-solution, water and brine and dried over Na$_2$SO$_4$. Precipitation with a solution of HCl in ether yielded the title compound as the hydrochloride. M.p.: 241°–244° C.

$^1$H-NMR in d$_6$-DMSO [δ, ppm]: 2.80 (s,3H); 3.00 (m,2H); 3.31 (t,2H); 3.35– 3.67 (m,4H); 4.60 (t,2H); 4.77(d, 1H); 6.23 (s,1H); 7.26 (s,1H); 7.33 (s,1H); 10.00 (s,1H); 10.25 (broad s,2H); 10.00 (s,1H).

What is claimed is:

1. 2,3,4,5-tetrahydro-1H-3-benzazepines having the formula I

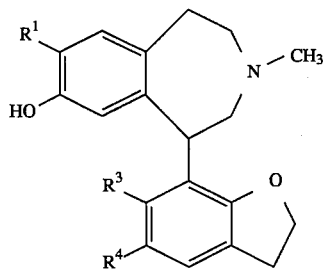

(I)

wherein

R$^1$ is Cl or Br;

R$^3$ and R$^4$ independently are hydrogen, halogen, CF$_3$, CN, NO$_2$ or NH$_2$ and all optical isomers thereof, and pharmaceutically acceptable acid addition salts thereof, provided that R$^3$ and R$^4$ cannot be hydrogen at the same time.

2. The compound according to claim 1 wherein R$^1$ is Cl.

3. The compound according to claim 1 in which said compound is selected from the group consisting of (+)-8-chloro-5-(5-bromo- 2,3-dihydrobenzofuran-7-yl)-7-hydroxy-3-methyl-2,3,4,5-tetrahydro-1H-3-benzazepine, (+)-8-chloro-5(2,3-dihydro-5-iodo-benzofuran-7-yl)-7-hydroxy-3-methyl- 2,3,4,5-tetrahydro-1H-3-benzazepine, (+) 8-chloro-5(5,6-dichloro-2,3-dihydrobenzofuran-7-yl)-7-hydroxy-3-methyl-2,3,4,5-tetrahydro-1H-3-benzazepine, (+) 8-chloro-5(5-chloro-2,3-dihydrobenzofuran-7-yl)-7-hydroxy-3-methyl- 2,3,4,5-tetrahydro-1H-3-benzazepine, 8-chloro-5(5-nitro-2,3-dihydrobenzofuran-7-yl)-7-hydroxy-3-methyl- 2,3,4,5-tetrahydro-1H-3-benzazepine and 8-chloro-5(5-amino-2,3-dihydrobenzofuran-7-yl)-7-hydroxy-3-methyl- 2,3,4,5-tetrahydro-1H-3-benzazepine.

4. A pharmaceutical composition comprising the compound of claim 1 or a pharmaceutically acceptable acid addition salt thereof and a pharmaceutically acceptable carrier or diluent.

5. The pharmaceutical composition according to claim 4 wherein said compound is in the form of an oral dosage unit containing about 0.1–100 mg of the active compound.

6. A method of treating a mental disorder relating to a dysfunction of a dopamine D-1 receptor in a person in need of such treatment characterized in administering to said person an amount of a compound according to claim 1 effective in alleviation of such an ailment.

7. A method of treating a mental disorder relating to a dysfunction of a dopamine D-1 receptor in a subject in need of such treatment comprising the step of administering to said subject an amount of the composition according to claim 4, which is effective for the alleviation of such ailment.

* * * * *